United States Patent [19]

Aves

[11] Patent Number: 5,740,791
[45] Date of Patent: Apr. 21, 1998

[54] RETRACTING ORAL AIRWAY

[75] Inventor: Teodulo Aves, Woodlands, Tex.

[73] Assignee: Board of Regents, The University of Texas System, Austin, Tex.

[21] Appl. No.: 638,385

[22] Filed: Apr. 26, 1996

[51] Int. Cl.$^6$ .............................................. A61M 16/00
[52] U.S. Cl. ................... 128/200.26; 128/207.14; 600/215
[58] Field of Search .................. 128/200.26, 207.14, 128/206.29, 912, DIG. 26; 600/196, 215

[56] References Cited

U.S. PATENT DOCUMENTS

| | | | |
|---|---|---|---|
| 2,474,857 | 7/1949 | Newman | 600/215 |
| 3,384,078 | 5/1968 | Gauthier | 600/215 |
| 3,749,088 | 7/1973 | Kohlmann | 600/215 |
| 4,064,873 | 12/1977 | Swenson | 600/215 |
| 4,112,936 | 9/1978 | Blachly | 128/206.29 |
| 4,213,451 | 7/1980 | Swenson | 600/215 |
| 4,337,761 | 7/1982 | Upsher | 600/196 |
| 4,848,331 | 7/1989 | NorthwayMeyer | 128/200.26 |
| 4,982,729 | 1/1991 | Wu | 128/200.26 |
| 5,024,218 | 6/1991 | Ovassapian et al. | 128/200.26 |
| 5,183,031 | 2/1993 | Rossoff | 600/131 |
| 5,203,320 | 4/1993 | Augustine | 128/207.14 |
| 5,253,643 | 10/1993 | Price | 128/207.14 |
| 5,261,392 | 11/1993 | Wu | 128/200.26 |
| 5,287,848 | 2/1994 | Cubb et al. | 128/200.26 |
| 5,353,787 | 10/1994 | Price | 128/200.26 |
| 5,501,654 | 3/1996 | Failla et al. | 600/215 |
| 5,584,795 | 12/1996 | Valenti | 600/196 |

OTHER PUBLICATIONS

Fitzgerald, et al., "Excursions of the cervical spine during tracheal intubation: blind oral intubation compared with direct laryngoscopy," *Anaesthesia* 49:111–115, Feb. 1994.

Childres, "New Method for Fiberoptic Endotracheal Intubation of Anesthetized Patients," *Anesthesiology* 55:595–596, 1981.

Abstract from Computer search dated Jan. 19, 1996 –Krafft, et al., "A New Device for Blind Oral Intubation in Routine and Difficult Airway Management," *Eur. J. Anaesthesiology* 11:207–212, May 1994.

*Primary Examiner*—Aaron J. Lewis
*Attorney, Agent, or Firm*—Akin, Gump, Strauss, Hauer & Feld, L.L.P.

[57] ABSTRACT

An adjustable retracting oral airway for reversibly establishing a maximum flange-blade dimension of the distal portion of an intra-oral extension with respect to a dental flange. Several alternative extension retraction means coupled to a dental flange are used to establish varying degrees of freedom of motion of the intra-oral extension (including the blade) with respect to the flange. Mating surfaces of the blade extension and the extension retraction means may be frictional or may have positive interlock (as, for example, with ratchet or gear teeth). Living hinges of plastic material are used in low-cost embodiments, including an embodiment having a single wedge-lock hinge. Self-coiling tension members are found in low-profile embodiments allowing mask ventilation with a retracting oral airway in place.

8 Claims, 5 Drawing Sheets

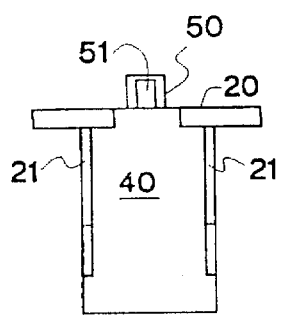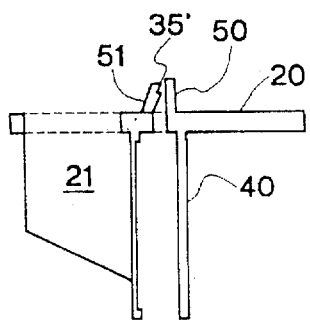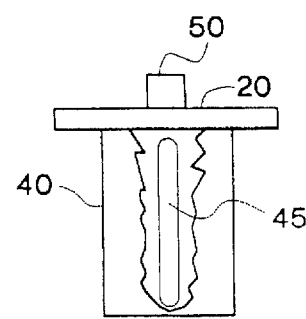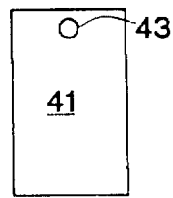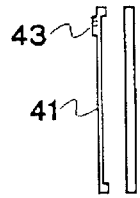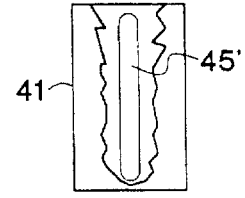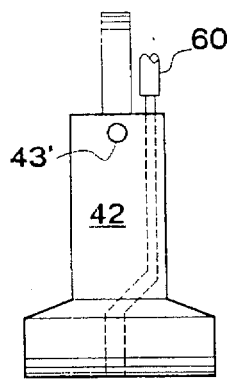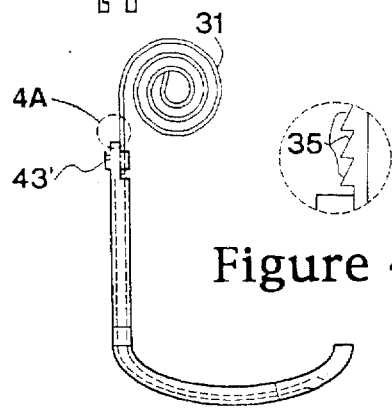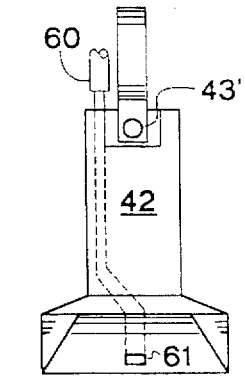
Figure 3        Figure 4        Figure 5
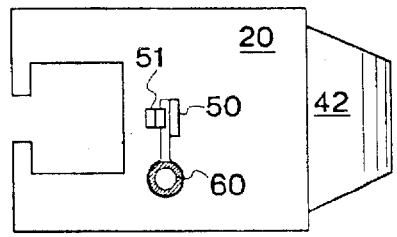
Figure 6

5,740,791

RETRACTING ORAL AIRWAY

BACKGROUND

1. Field of the Invention

The invention relates to methods and apparatus for supporting and controlling ventilation in a patient, and in particular for establishing and/or maintaining an open airway.

2. Airway Management

Ventilation and oxygenation of patients who require assistance in breathing, such as those undergoing general anesthesia, are frequently provided with oxygen-enriched gas mixtures administered via an oro-nasal mask or an oral endotracheal tube. During mask ventilation, an oral airway is often placed in the patient's mouth to prevent the soft tissues of the mouth and oropharynx from collapsing into and obstructing the airway. Commercially available oral airways often comprise a dental flange that preferably rests on the teeth and/or lips, with an elongated intra-oral extension having a distal curve (i.e., the blade) to fit substantially posterior to the tongue. The dental flange often incorporates or is coupled to at least one relatively solid structure (a bite block) which extends far enough into the oropharynx to prevent clenching of the teeth on structures such as an endotracheal tube, a suction catheter, or a fiberoptic laryngoscope which may be passed into the oropharynx while the oral airway is in place.

During mask ventilation, the intra-oral extension is intended to prevent the tongue of a supine anesthetized patient from completely blocking ventilation by obstructing the oropharynx. Besides their use during mask ventilation, oral airways can also protect an endotracheal tube from kinking due to contraction of the patient's jaw muscles and can help stabilize endotracheal tube position in the trachea. Additionally, an oral airway can facilitate insertion of a fiberoptic laryngoscope to assist in endotracheal tube placement by providing a relatively clear passage around the tongue.

In some patients, however, control of tongue position with a commercially available oral airway is insufficient to maintain an open airway and/or to provide sufficient clearance for fiberoptic laryngoscopy. Occasionally, an anesthetist will determine after intravenous administration of an anesthetizing dose of an induction agent that a patient is both impossible to intubate and impossible to mask ventilate. Emergency surgical intervention is then required to prevent death, but even when death is averted substantial morbidity and excess costs may result.

If a wide selection of oral airway sizes and shapes were readily available, the incidence of the above emergencies could probably be reduced or even substantially eliminated. But to minimize equipment costs, oral airways are usually provided in a limited selection of common shapes and sizes as disposable items. In attempting to fit one of these devices to an individual patient, the distance from the dental flange to the distal curved blade of the intra-oral extension (that is, the flange-blade dimension) may be found to be incorrect, resulting in either excessive or insufficient retraction of the base of the tongue for optimal visualization of the vocal cords and/or free passage of air. Additionally, protruding teeth and/or a prognathous or receding jaw may leave the dental flange in contact with only the upper or lower teeth, gums and/or lips, increasing the likelihood of excessive tissue pressures and consequent tissue injury. An improved oral airway would provide effective tongue retraction for ventilation and/or laryngoscopy while minimizing tissue pressures, adjustably accommodating a variety of spatial relationships among the anatomic structures of the oropharynx.

SUMMARY OF THE INVENTION

The present invention includes a retracting oral airway comprising a substantially planar dental flange and an elongated intra-oral extension. The intra-oral extension, in turn, comprises a distal curved blade portion and a proximal portion. The proximal portion of the intra-oral extension comprises extension retraction means through which the maximum flange-blade dimension may be adjusted (and then reversibly locked via lock means) by changing the length of the airway intra-oral extension within the oropharynx. To accomplish this extension length adjustment, the extension retraction means comprises at least first and second slidingly adjustable segments (one of which is coupled to the dental flange), together with displacement stop means to prevent disconnection of the segments and lock means to reversibly lock the segments for preventing elongation of the extension retraction means beyond a predetermined point (thus reversibly establishing a maximum flange-blade dimension). Optionally, beating means coupling the dental flange and intra-oral extension may facilitate adjustment of the angular orientation of the intra-oral extension with respect to the airway's dental flange.

Establishment of a preferred flange-blade dimension can be accomplished by slidingly adjusting (that is, moving) a second segment (for example, a slotted elongated bar) with respect to a first segment (for example, a substantially plane anchoring surface coupled to the dental flange and having a locking stud passing through the bar slot and secured by a lock nut). In this case, the locking stud and lock nut act as displacement stop means when the lock nut is loosened to allow sliding movement of one segment with respect to another, while the locking stud, lock nut and anchoring surface act together as lock means when the lock nut is reversibly tightened to prevent sliding motion of one segment with respect to another. Note that in such embodiments, the slotted elongated bar may be manually grasped and adjusted (after loosening the lock nut) to establish a desired flange-blade dimension, after which the slotted bar may be (reversibly) locked in place.

An alternative embodiment of the retracting oral airway extension retraction means comprises at least first and second substantially coaxial telescoping (and slidingly adjustable) segments. One such telescoping segment (for example, the first) is coupled to the dental flange, while another telescoping segment (for example, the second) fits slidingly within the first segment. Relative movement of such first and second telescoping segments (or any two telescoping segments in sliding contact) is preferably constrained by displacement stop means comprising, for example, at least one stop pin which rises above a sliding contact surface (of either of two corresponding surfaces in sliding contact) to fit slidingly into a groove or slot within the other corresponding sliding contact surface of an adjacent telescoping segment. An alternative form of displacement stop means may comprise, for example, corresponding interfering flanges on adjacent telescoping segments which prevent extension of said telescoping segments beyond the point at which the flanges touch each other.

For embodiments of the retracting oral airway comprising two or more slidingly adjustable telescoping segments, displacement stop means may comprise one or more such pin-groove combinations on corresponding (that is, slidingly mating) adjacent telescoping segments. Such displacement stop means establish a maximum flange-blade dimension by limiting elongation of the extension retraction means, but for applications wherein a flange-blade dimension short of the maximum is desired, preferred embodiments of the extension retraction means additionally comprise at least one flexible tension member having a distal portion and a proximal portion, the distal portion of which is coupled to the distal curved blade portion of the intra-oral extension and which passes proximate (preferably through an opening or slot in) the dental flange and which can preferably be reversibly coupled thereto by lock means capable of holding the distal portion of the tension member in tension. Note that the locking stud, lock nut and anchoring surface described above as acting together as lock means when the lock nut is reversibly tightened can hold the distal portion of the (slotted bar) tension member in tension. Similar lock means can maintain desired tension even in a substantially smooth string, cable or ribbon-like tension member which is reversibly clamped between the anchoring surface and the lock nut.

But because the flexible tension member may take a variety of forms (including a semi-rigid bar), lock means may also vary in form. For example, a flexible tension member may comprise a thin string or cable knotted at intervals. An adjustable degree of tension may be maintained on the distal portion of such a tension member by reversibly placing the string or cable into a slot in the dental flange which has sufficient width to accommodate the string or cable diameter but is too narrow to allow passage of the knots. Similarly, the flexible tension member may comprise a plurality of tooth-like protrusions along its length (as in a ratchet), such protrusions being reversibly engaged as desired by corresponding protrusions on (or coupled to) the dental flange. A mechanism analogous to the latter embodiment may be found on common plastic cable ties which employ tooth-like projections along the elongated portion of the tie, together with a lock portion having corresponding (mating) tooth-like projections within a wedge-lock means portion designed to accept insertion of the elongated portion (but usually not its withdrawal). While the toothed elements of many cable ties can not be easily disengaged after the elongated portion is inserted in the lock portion, disengagement and/or adjustment of an analogous wedge-lock means in the present invention may be facilitated by a slot-like structure as described above which allows substantially lateral engagement and disengagement of an elongated (toothed) flexible tension member between two wedge-lock wedging structures, at least one such wedging structure comprising one or more correspondingly toothed structures. Another analogous wedge-lock means preferred in certain embodiments of the present invention is similar to that above except that corresponding toothed structures are replaced by corresponding frictional surfaces. Such frictional surfaces impart sufficient frictional drag force on the tension member between them to maintain a preset maximum flange-blade dimension in use, while allowing adjustment of this dimension as desired through manual force applied to the tension member.

While an elongated flexible tension member may take the form of a string or cable as noted above, a preferred embodiment of the tension member is a self-coiling ribbon. Such a ribbon may incorporate the tooth-like projections described above as part of the lock means, or a substantially smooth ribbon form of tension member may be reversibly locked to an anchoring surface using a locking stud and lock nut as above. Regardless of the lock means employed, the proximal portion of a self-coiling ribbon flexible tension member (which is not in tension and which is separated from the distal portion, which is in tension, by the lock means) will preferably spontaneously assume a relatively compact coiled form adjacent to the dental flange of a retracting oral airway. When desirable to facilitate tight coiling and/or to aid proper tensioning of the tension member, the coiled form may be coiled about a core or winding axle having convenient finger grips. Any such compact low-profile form of the retracting oral airway allows an oro-nasal mask to be placed on a patient while a retracting oral airway is in place. Proper adjustment of the maximum flange-blade dimension then facilitates mask ventilation of the patient.

Besides facilitating mask ventilation, its adjustability facilitates easy insertion of the retracting oral airway in a patient's oropharynx, thereby tending to reduce soft tissue injuries. Additionally, a custom fitting of the airway to each patient can ensure the desired maximum flange-blade dimension and, optionally, an optimal angular relationship of the intra-oral extension with respect to the dental flange. Such custom fitting may preferably be facilitated by imparting a tension-dependent bending compliance (that is, degree of bending per unit of applied transverse load) to slidingly adjustable telescopic segments of the extension retraction means. Such tension-dependent bending compliance is greatest when tension is least (as when the airway is first inserted), and bending compliance is then progressively reduced as tension is applied through an elongated tension member. Such progressively reduced bending compliance allows the retracting oral airway to initially accommodate a wide variety of spatial relationships among anatomic structures in an individual patient's oropharynx (thus avoiding excessive localized tissue pressure which over time can lead to tissue necrosis), while later exhibiting sufficient rigidity for effective tongue retraction.

Thus, a preferred embodiment of a retracting oral airway comprises an elongated intra-oral extension having a substantially straight proximal portion and a substantially curved distal portion. Additionally, the airway comprises a substantially planar dental flange adjustably coupled substantially transversely to the proximal portion of the intra-oral extension. Finally, extension retraction means coupled to the dental flange are adjustably coupled to the extension to adjustably limit longitudinal displacement of the extension with respect to the flange (thus limiting the flange-blade dimension).

Note that in many preferred uses of the invention, any rotation of the intra-oral extension with respect to the dental flange which may be allowed will preferably be within the sagittal plane (as the airway is normally placed in a patient's oropharynx). The preferred embodiments of the invention described above substantially limit rotation of the elongated intra-oral extension about its own proximal portion longitudinal axis with respect to the dental flange by matching a substantially rectangular cross-sectional shape in the extension (including adjustable segments thereof) with a flange-coupled segment, a rectangular hole in the flange, and/or a corresponding plane anchoring surface within or coupled to the dental flange through which the extension protrudes. However, in instances where the airway is intended to be placed off-center (such as where the patient's anatomy has been altered by surgery, accident or disease), a round cross-sectional shape (as, for example, in corresponding adjustable telescopic segments) may be chosen for the extension. A corresponding substantially round hole is then preferably provided in the dental flange, accompanied by extension retraction locking means comprising, for example, an arbortype clamp coupled to the dental flange for maintaining the desired spatial relationship of the proximal portion of the extension to the dental flange. In such an embodiment of the airway, rotation of the extension about its proximal portion longitudinal axis with respect to the dental flange may be predetermined or may be adjusted after the retracting oral airway is inserted in a patient's oropharynx.

Alternatively, the invention includes a method of fitting a retracting oral airway to a patient. The method comprises placing an elongated intra-oral extension having a substantially straight proximal portion and a substantially curved distal portion within the patient's oropharynx, the curved distal portion extending at least partially around said patient's tongue. One then adjusts the extension retraction means to exert tension on the distal portion of the intra-oral extension for retracting the patient's tongue.

Because of the optionally modular construction of the retracting oral airway, a variety of special dental flanges may be matched with suitable intraoral extensions in the operating room for custom-fitting individual patients. One such special dental flange comprises cushion means having a relatively soft surface layer material (such as soft rubber or plastic) on gum-contacting surfaces of one or more intra-oral gum rests. Gum rests can have a predetermined shape approximating that of the opposing gums, or gum rests can be custom-fitted to a patient to accommodate malpositioned teeth or other unique anatomic features.

Because of the variety of extension retraction means usable for special purposes, the invention includes several methods of coupling an intra-oral airway extension to a dental flange. One method comprises locating at least a portion of the extension retraction means between at least one pair of complementary opposing gripping blocks hinged to the dental flange and (optionally) clamping the extension retraction means portion between the opposing gripping blocks with a retraction clamp means. Note that the gripping blocks, when hinged to the dental by living hinges (comprising relatively elongated and relatively thin and flexible portions of a plastic or rubber material used to construct the dental flange) may exert sufficient self-closing force on the extension to maintain engagement of corresponding tooth-like structures on the extension and at least one gripping block, thus maintaining sufficient tension on the intro-oral extension so that application of clamp means is not necessary.

BRIEF DESCRIPTION OF THE DRAWINGS

FIG. 3 schematically illustrates an exploded rear view of a retracting oral airway employing a ribbon-shaped flexible tension member and rectangular telescoping segments.

FIG. 4 schematically illustrates an exploded side view in cross-section with detail of a retracting oral airway employing a ribbon-shaped flexible tension member and rectangular telescoping segments.

FIG. 5 schematically illustrates an exploded frontal view of a retracting oral airway employing a ribbon-shaped flexible tension member and rectangular telescoping segments partially cut away to illustrate displacement stop means slots.

FIG. 6 schematically illustrates a top view of the retracting oral airway of FIG. 5.

DETAILED DESCRIPTION

Figure 1:
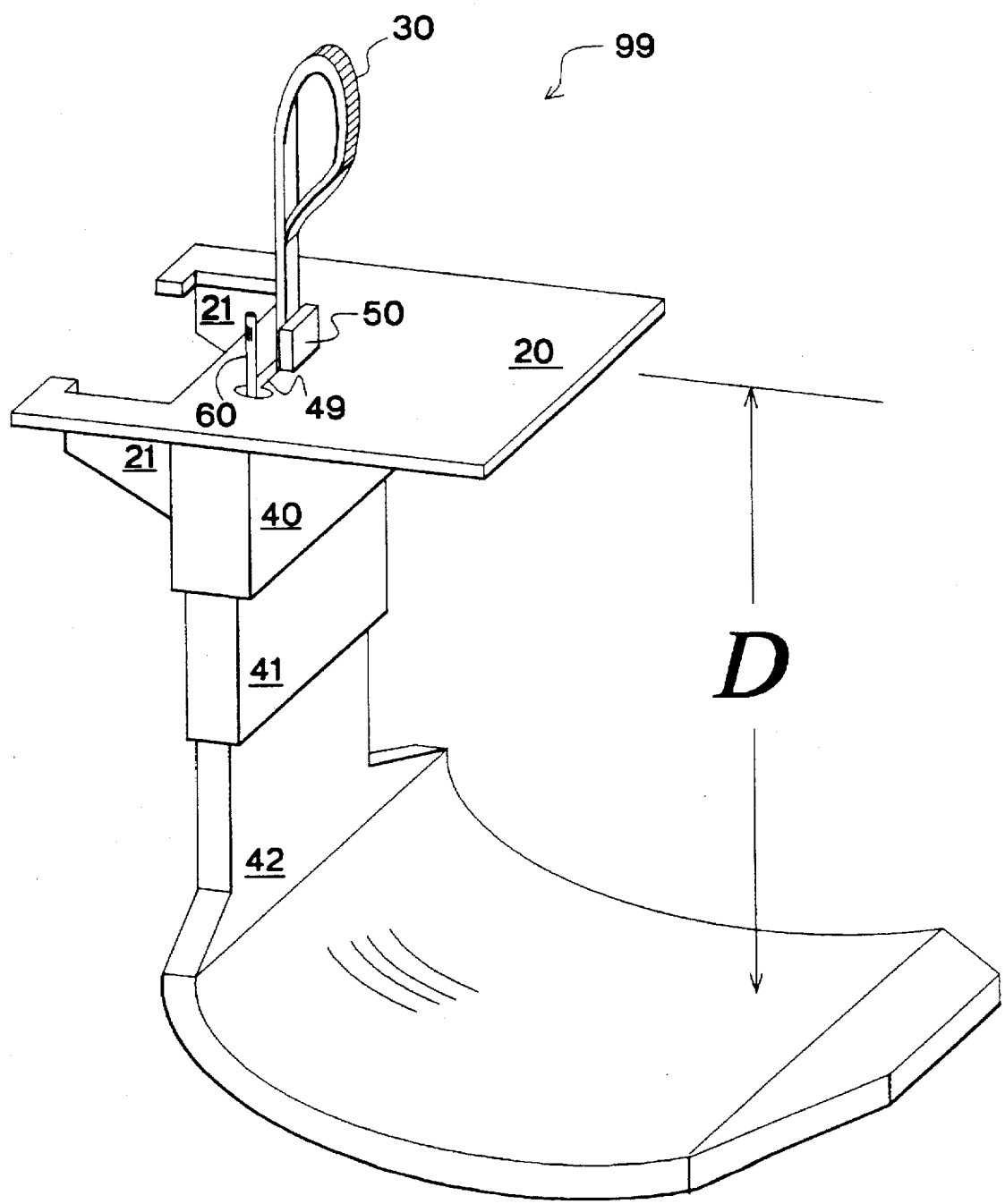
FIG. 1 schematically illustrates an isometric view of a retracting oral airway employing a ribbon-shaped flexible tension member and extended rectangular telescoping segments.
Figure 2:
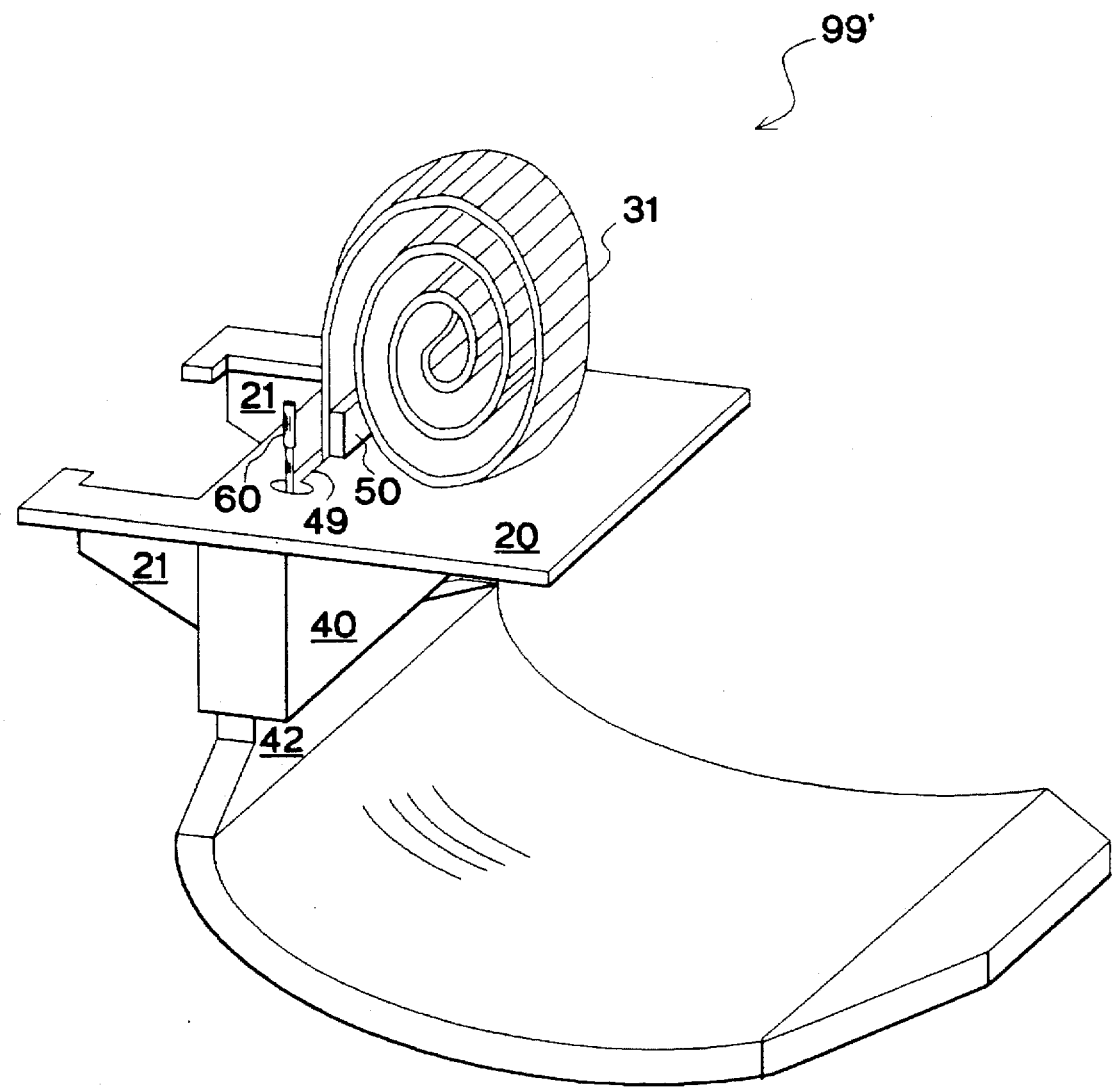
FIG. 2 schematically illustrates an isometric view of a retracting oral airway employing a self-coiling ribbon-shaped flexible tension member and retracted rectangular telescoping segments.

Preferred embodiments of the invention 99,99' as illustrated in FIGS. 1 and 2 include ribbon-shaped elongated flexible tension members 30,31, the distal ends of which are coupled to distal curved blade portions 42. The (rectangular) proximal end of blade portion 42 telescopes into rectangular slidingly adjustable segment 41, which in turn telescopes into rectangular slidingly adjustable segment 40. Segment 40 is coupled to dental flange 20 (as by gluing or welding), as are bite blocks 21. Dental flange 20,20',20" also preferably includes a slot 55 to facilitate insertion of, for example, an endotracheal tube and/or a fiberoptic laryngoscope into a patient's oropharynx. The telescoping action of slidingly adjustable segments changes flange-blade dimension D (see FIG. 1), with maximum dimension D preferably being determined in use by flexible tension members 30,31. Note that adjacent telescoping segments are prevented from being disconnected by displacement stop means comprising stop pins 43,43' which slide within grooves 45,45' respectively. Suction line 60, which extends at least partly through blade portion 42 with at least one suction port 61 open within the oropharynx, may optionally be included in retracting oral airways of the present invention.

Figure 11:
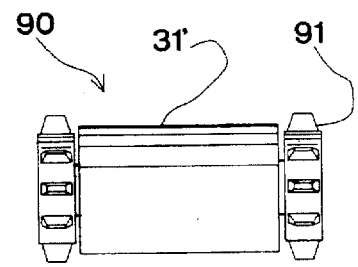
FIG. 11 schematically illustrates a winding axle assembly which may optionally be used to compactly coil and/or tension a ribbon-shaped flexible tension member as illustrated in FIG. 10.
Figure 10:
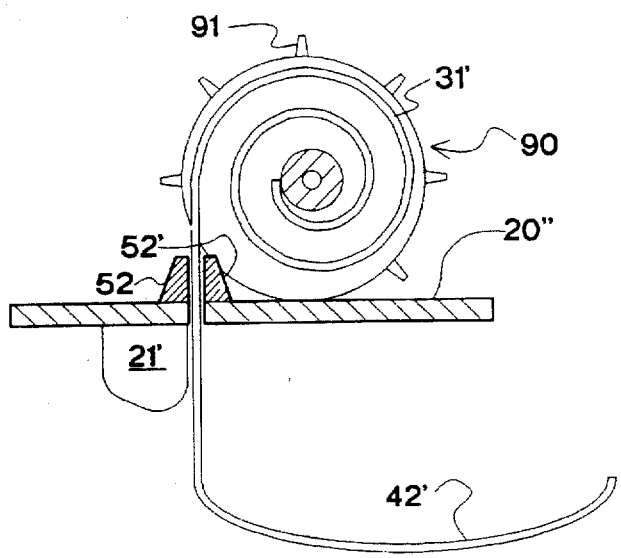
FIG. 10 schematically illustrates a side view of a retracting oral airway employing a ribbon-shaped flexible tension member and frictional lock means for maintaining tension in the distal tension member.
Figure 12:
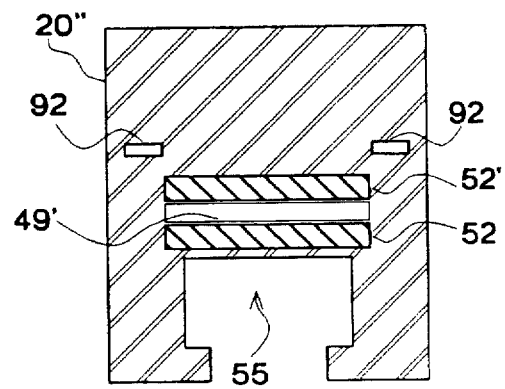
FIG. 12 schematically illustrates a plan view of a dental flange for the retracting oral airway of FIG. 10.

Flexible tension members 30,31 differ in that member 31 is a self-coiling ribbon while member 30 is not self-coiling but has a proximal loop to facilitate manual application of tension. Note that the proximal end of any flexible tension member may preferably be wound on an axle assembly 90 having finger grips 91 (shown in transverse cross-section in FIG. 10 and in side elevation in FIG. 11) for convenience in tensioning the member and for storing the proximal portion of the member in a compact form. To reversibly lock flexible tension member 31' to maintain tension on a distal portion of tension member 31', any two substantially aligned finger grips 91 may be reversibly inserted into corresponding slots 92 in dental flange 20" (see FIGS. 10–12). Tension on a distal portion of tension member 31' will then tend to rotate axle assembly 90 (in a counterclockwise direction as illustrated in FIG. 10). This rotation will tend to be blocked by guide bar 52' as tension member 31' passes (in tension) between guide bars 52,52' (see FIG. 10).

Note that whereas tension member 31' can be substantially smooth if it is firmly coupled (as by friction and/or gluing or welding) to axle assembly 90, but both tension members 30,31 comprise a plurality of tooth structures 35, as seen in detail in FIG. 4. Note also that flexible tension members 30,31 pass through lock means which are wedge-lock means, comprising two wedging structures 50,51 coupled (as by welding or gluing) to dental flange 20, with wedging structure 51 comprising at least one toothed structure 35'. Tension members 30,31 can optionally be moved laterally within slot 49 to either engage the lock means or disengage from the lock means.

Figure 9:
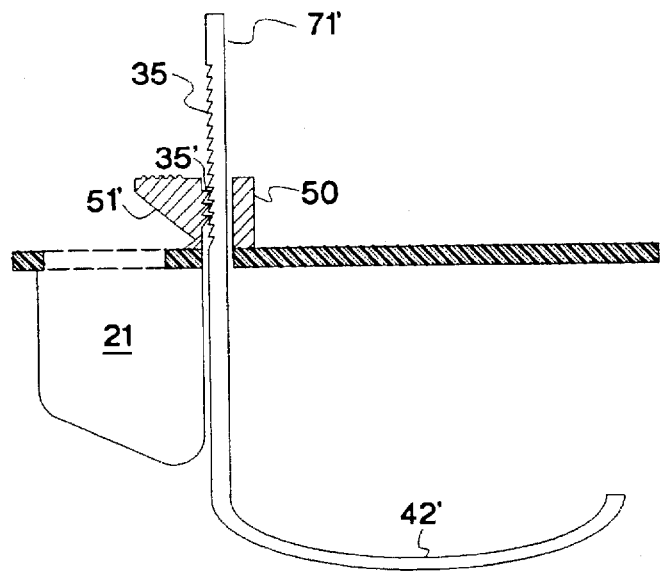
FIG. 9 schematically illustrates a side view of a retracting oral airway employing a toothed bar tension member and wedge-lock lock means for maintaining tension in the distal tension member.

Analogously, semirigid tension member 71' (see FIG. 9) also passes through wedge-lock means comprising two wedging structures 50,51', wherein structure 51' is preferably a stronger structure than structure 51 and comprises a plurality of toothed structures 35'. Also note that structure 51' is hinged to dental flange 20 and so shaped that increased tension in tension member 71' tends to engage tooth structures of structure 51' more tightly with tooth structures 35 on tension member 71'.

Figure 7:
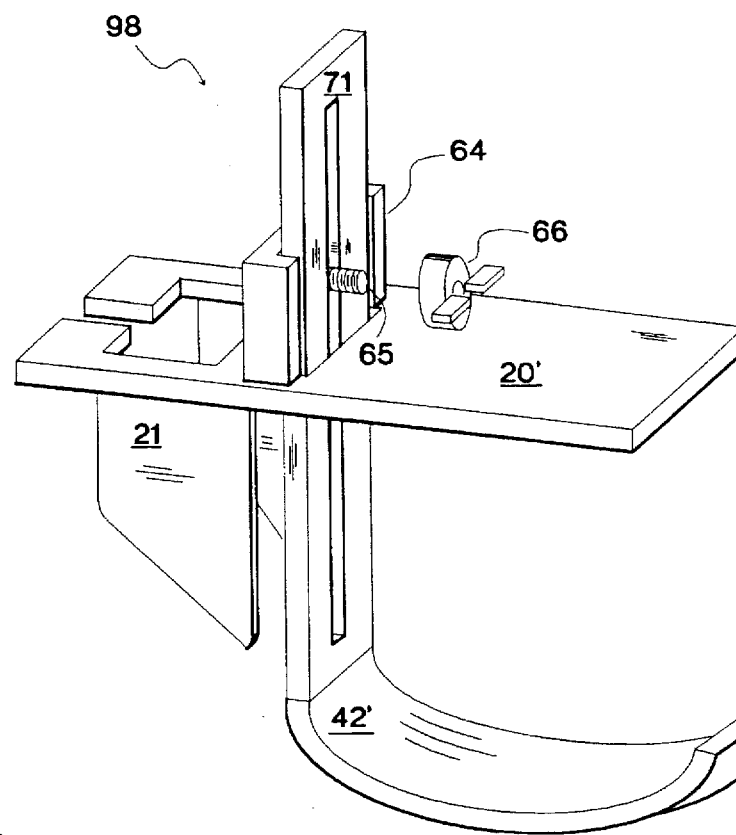
FIG. 7 schematically illustrates an isometric view of a retracting oral airway employing a slotted bar tension member with locking stud and lock nut.
Figure 8:
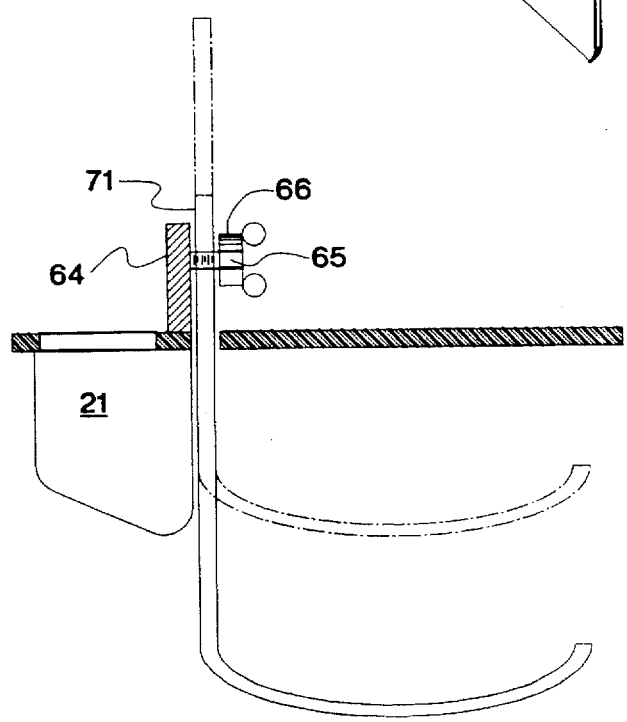
FIG. 8 schematically illustrates a side view of the retracting oral airway of FIG. 7 showing the blade in extended and retracted positions.

An embodiment 98 of the retracting oral airway employing a slotted bar tension member 71 is illustrated in FIGS. 7 and 8. Note that dental flange 20' differs from dental flange 20 because of the substantially rectangular slot required to allow passage of slotted bar 71, as well as the coupled slidingly adjustable segment 64 which is coupled (as by gluing or welding) to the flange 20'. With lock nut 66 loosened on locking stud 65, free sliding relative motion between slotted bar 71 and segment 64 is allowed, whereas tightening lock nut 66 reversibly fixes the relative positions of blade portion 42' and dental flange 20'. FIG. 8 schematically illustrates two such relative positions.

What is claimed is:

1. A retracting oral airway, comprising
   a substantially planar dental flange;
   an elongated intra-oral extension having a distal curved blade portion and a proximal portion, said proximal portion comprising extension retraction means and said extension retraction means comprising
      at least first and second slidingly adjustable segments, which are selectively adjustable by said extension retraction means said first segment being coupled to said dental flange;
      displacement stop means to prevent disconnection of said slidingly adjustable segments; and
      lock means to reversibly lock said slidingly adjustable segments to establish a maximum dimension between said dental flange and said distal curved blade portion.

2. The retracting oral airway of claim 1 wherein said slidingly adjustable segments are telescopic.

3. The retracting oral airway of claim 2 wherein said telescopic slidingly adjustable segments have a substantially rectangular cross-section.

4. The retracting oral airway of claim 1, wherein the extension means additionally comprises at least one elongated flexible tension member having a distal portion and a proximal portion, said distal portion being coupled to said distal curved blade portion of said intra-oral extension, and said proximal portion passing proximate said dental flange.

5. The retracting oral airway of claim 4 wherein said at least one elongated flexible tension member is a self-coiling ribbon.

6. The retracting oral airway of claim 5 wherein said extension retraction means comprises at least one gripping block hinged to said dental flange and wherein said extension and said at least one gripping block comprise tooth-like projections on corresponding surfaces.

7. The retracting oral airway of claim 1 wherein said lock means comprises a locking stud, lock nut and substantially plane anchoring surface for reversibly and adjustably fixing said intra-oral extension to said dental flange.

8. A method of preparing a patient for mask ventilation, comprising:
   providing a substantially planar dental flange having an elongated intro-oral extension having a distal curved blade portion and a proximal portion, said proximal portion comprising extension retraction means and said extension retraction means comprising at least first and second slidingly adjustable segments which are selectively adjustable by said extension retraction means, said first segment being coupled to said dental flange; displacement stop means to prevent disconnection of said slidingly adjustable segments; and lock means to reversibly lock said slidingly adjustable segments to establish a maximum dimension between said dental flange and said distal curved blade portion;
   inserting said elongaged intra-oral extension within a patient's oropharynx, and placing said curved distal portion at least partially around the patient's tongue;
   adjusting said extension retraction means to exert tension on said intra-oral extension distal portion for retracting the patient's tongue; and
   applying an oral nasal mask to the patient to prepare the patient for mask ventilation.

* * * * *